United States Patent [19]

Rosin et al.

[11] Patent Number: 4,948,807
[45] Date of Patent: Aug. 14, 1990

[54] PHENYL CARBAMATES

[75] Inventors: Marta W. Rosin; Michael Chorev; Zeev Tashma, all of Jerusalem, Israel

[73] Assignee: Proterra AG, Zug, Switzerland

[21] Appl. No.: 320,700

[22] Filed: Mar. 8, 1989

Related U.S. Application Data

[63] Continuation of Ser. No. 185,451, Apr. 25, 1988, abandoned, which is a continuation of Ser. No. 835,466, Mar. 3, 1986, abandoned.

[30] Foreign Application Priority Data

Mar. 5, 1985 [IL] Israel ........................................ 74497

[51] Int. Cl.$^5$ .................. C07C 125/067; A61K 31/27
[52] U.S. Cl. ...................................... 514/484; 514/330; 514/487; 514/490; 514/237.5; 544/162; 546/226; 560/32; 560/115; 560/136
[58] Field of Search ...................... 560/115, 163, 136; 514/484, 490, 487

[56] References Cited

U.S. PATENT DOCUMENTS

| | | | |
|---|---|---|---|
| 1,905,990 | 4/1933 | Aeschlimann | 560/32 |
| 2,208,485 | 7/1940 | Aeschlimann | 560/136 |
| 2,362,508 | 11/1944 | Stevens | 560/136 |
| 2,493,710 | 1/1950 | Aeschlimann | 560/136 |

FOREIGN PATENT DOCUMENTS 1037753  7/1956  Fed. Rep. of Germany ...... 560/136

OTHER PUBLICATIONS

Stedman, Biochemical Journal, 20 pp. 719–734 (1926).
Wasserman, Proc. Natl. Acad. Sci., U.S.A., 79 pp. 4810–4814 (1982).
Weiden, J. Agr. Food Chem., 13 pp. 200–204 (1965).
Berry, Biochem. Pharmacol., 20 pp. 3236–3238 (1971).
Weinstock, Advances in Behavioral Biology, 29 pp. 539–549 (1986).
Lange, Haemostasis, 10 pp. 315–347 (1981).
Meltzer, Entomol. Exp. App., 12 pp. 169–182 (1969).

Primary Examiner—Michael L. Shippen
Attorney, Agent, or Firm—Ribis, Graham, Verdon & Curtin

[57] ABSTRACT

Phenyl carbamates of the general formula

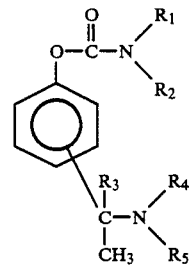

wherein $R_1$ to $R_5$ are as defined in the claims, are useful as pharmaceuticals.

4 Claims, No Drawings

PHENYL CARBAMATES

This application is a continuation of application Ser. No. 185,451, filed on 04/25/88, entitled Phenyl Carbamates which in turn was a continuation of application Ser. No. 835,466 filed Mar. 3, 1986, both now abandoned.

The present invention relates to novel phenyl carbamates which are useful as pharmaceutical compositions. The invention further relates to pharmaceutical compositions having anticholinesterase activity.

Acetylcholine is a major neurotransmitter which is found in all parts of the body. Any reduction in its activity, either as a result of neuronal damage, degeneration etc. or as induced by drugs or toxins, causes marked changes in the function of the organism. Acetylcholine itself has an extremely short half life, since it is rapidly hydrolysed at its site of action and in plasma by specific cholinesterase enzymes. Drugs that inhibit acetylcholinesterase, markedly increase and prolong the action of acetylcholine, thereby enhancing cholinergic transmission. Three such agents are used clinically, i.e., physostigmine, a naturally occurring alkaloid, and two synthetic analogues, neostigmine and pyridostigmine. The latter two agents are strongly ionised at physiological pH and therefore are only poorly absorbed from the gastro-intestinal tract, and do not penetrate the central nervous system to any significant extent. Physostigmine is absorbed after oral administration and readily enters the brain. As a therapeutic agent it has several disadvantages. It is chemically unstable and must be prepared in solution with an antioxidant, and protected from light. It has a relatively short half-life (20–40 mins) thereby necessitating frequent administration. The latter is of particular importance when the drug is to be administered chronically. It has a low therapeutic ratio, a value of 3–5 being reported in the majority of studies in laboratory animals, and a small therapeutic window, i.e. small range of dose in which it can be given without the accompaniment of side effects. Although physostigmine is absorbed from the gastrointestinal tract, this is reported to be irregular and unpredictable, and therefore it is usually preferred to administer the drug parenterally. This is a serious drawback if it is to be used chronically on an outpatient basis.

There are a number of clinical and pathological conditions which are associated with cholinergic underactivity which can be improved by the administration of an anticholinesterase agent. These include reduction in cholinergic transmission induced by a variety of exogenous substances acting in the peripheral, or central nervous system. Peripherally acting agents are gallamine, d-tubocurarine and pancuronium, which are used as muscle relaxants. Their action can readily be overcome by an anticholinesterase drug. Drugs which interfere with central cholinergic transmission are numerous, anticholinergic, atropine-like drugs including antiparkinson drugs, tricyclic antidepressants, neuroleptics, opiate analgesics, benzodiazepines and some types of general anaesthetics. So far the only agent that has proved to be of any value in reversing the effects of the latter group of drugs is physostigmine. In all reported cases of drug overdose or lack of recovery when the agent was used peri-operatively, physostigmine is usually administered parenterally, and administration is repeated every 20–30 minutes as required.

Chronic treatment with neuroleptics often results in tardive dyskinesias. The widespread use of agents having anticholinesterase activity for the treatment of schizophrenia makes this side effect an ever increasing possibility. Physostigmine injected intravenously produces a significant but short lived improvement in a proportion of patients.

A number of pathological and degenerative diseases has also been shown to be associated with a reduction or loss of cholinergic transmission. This includes myasthenia gravis and Eaton Lambert syndrome in which there is an interference with neuromuscular transmission.

A selective loss of choline acetyltransferase (the enzyme that synthesises acetylcholine) has been found in specific brain regions of patients with pre-senile dementia of the Alzheimer type. These include the frontal and temporal cortex, hippocampus, amygdala, caudate nucleus, substantia innominata. Degeneration of cholinergic neurons in some of these areas appears to be associated with the aphasia, apraxia, agnosia and loss of short term memory that occurs in Alzheimer's disease. A similar type of dementia is also found in patients with Down's syndrome that survive to the age of 40 years and show similar cholinergic deficits. There is also a loss of cholinergic transmission in the caudate nucleus and putamen of patients with Huntingdon's chorea. Physostigmine injections have also been of some benefit in this condition. Treatment with a centrally acting anticholinesterase should also prove to be beneficial in Friedrich's ataxia.

There are two major classes of potent inhibitors of the enzyme cholinesterase. The first group was modelled primarily on the natural alkaloids physostigmine (a carbamate) and an inhibitor of cholinesterase, and d-tubocurarine, an antagonist of acetylcholine. The second group consists of various organophosphorus compounds, such as diisopropylfluorophosphonate, paraxon etc. The vast majority of the compounds of both these series were designed primarily as insecticides. In the first group of carbamate derivatives, almost all of the potent insecticides are monomethyl carbamates lacking a charged nitrogen function. This enables the molecule to penetrate rapidly the insect cuticle and fatty nerve sheath. The dimethyl derivatives are slightly less potent but are particularly toxic to houseflies and aphids. The monomethyl derivatives tend to be unstable in solution and hydrolyse readily at physiological pH. This greatly limits their biological action in mammals and makes them less suitable as pharmaceutical or therapeutic agents.

The organo-phosphorus group of compounds causes irreversible inhibition of cholinesterase and other serine containing enzymes, which, together with their high relative toxicity, virtually precludes their use in pharmaceutical preparations. The only exception is echothiopate, a quaternary ammonium organophosphorus compound, employed in eye drops for the treatment of glaucoma.

The synthetic anticholinesterase agents currently employed as pharmaceuticals all contain a charged nitrogen function and can be broadly classified into 3 groups.
  (1) Reversible inhibitors which contain a charged nitrogen function attached to an aromatic ring, e.g. edrophonium.
  (2) Dimethyl carbamates with an aromatic or heterocyclic ring containing a charged nitrogen, neostigmine, pyridostigmine.

(3) Bisquaternary structures, e.g. Demacarium, Ambenonium. These agents tend to be more selective inhibitors of acetylcholinesterase than butyrylcholinesterase, compared with the monoquaternary molecules.

The pharmaceutical application of the quaternary anticholinesterase agents is limited because of their poor penetration through cell membranes. They are therefore used for actions outside the central nervous system, and are usually given parenterally, since they are not reliably absorbed from the gastrointestinal tract. Edrophonium, neostigmine and pyridostigmine and the bisquaternary analogues are used in anesthetic practice for the reversal of the action of muscle relaxants. They are also used for the treatment of myasthenia gravis, and paralytic ileus.

Physostigmine is the only potent anti-cholinesterase agent which has been used clinically to treat conditions in which an elevation of brain acetylcholine activity is desired. These include, Alzheimer's disease, tardive dyskinesia, Down's syndrome and Huntingdon's chorea. Physostigmine is also used to reverse the effects of overdose of anticholinergic agents, anti-Parkinson drugs, benzodiazepines and opiate analgesics.

Physostigmine is a natural alkaloid extracted from calabar beans and the seeds of the vine Physostigma venenosum and has the formula

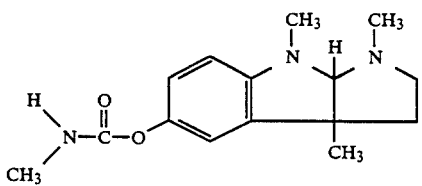

There is a need to provide new carbamate derivatives which show greater chemical stability than physostigmine.

Furthermore there is a need to provide new compounds which inhibit acetylcholinesterase in the brain for periods exceeding 3 hours but not more than 12 hours after a single administration.

There is also a need to provide new compounds which will be completely and reliably absorbed after oral administration.

There is also a need to provide new compounds which will be relatively less toxic than physostigmine. This means that the therapeutic ratio, defined as $$\frac{\text{dose to produce therapeutic effect}}{\text{dose to produce mortality in 50\% of animals}}$$

should be significantly higher than those of physostigmine and that the incidence and severity of side effects should be less than those of physostigmine at therapeutic doses.

There is also a need to provide new compounds which can be given orally or parenterally to treat chronic conditions in which it is desired to raise cholinergic activity in the central nervous system. These include, Alzheimer's disease, Down's syndrome, Huntingdon's chorea, Friedrich's ataxia.

There is also a need to provide compounds that can be given parenterally at the end of operations, and anesthetic procedures, to restore wakefulness, respiration and cardiovascular parameters to normal, after the use of anticholinergic, opiates, benzodiazepines, neuroleptics and general anaesthetics, thereby shortening the stay of patients in the recovery room.

There is also a need to provide compounds that can be given together with narcotic analgesics to patients suffering from severe pain, e.g. traumatic, post-operative, or due to carcinomatosis etc. in order to reduce the side effects (respiratory depression, somnolence, constipation and urinary retention) commonly encountered with narcotics, without impairing their analgesic potency.

There is also a need to provide compounds that can be given to patients receiving antipsychotic drugs, which have developed tardive dyskinesias, in order to diminish or abolish the latter syndrome, without exascerbating the psychosis.

According to the present invention it has now been surprisingly found that certain novel and known phenyl carbamates also inhibit acetylcholinesterase in the mammalian brain after administration to provide systemic activity, e.g. oral or parenteral administration.

Thus according to the present invention there is now provided a pharmaceutical composition adapted to produce anticholinesterase activity in the central nervous system of mammals comprising a compound of the general formula I

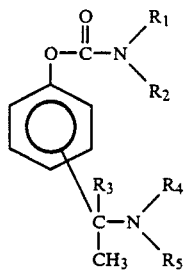

wherein
$R_1$ is hydrogen, lower alkyl, cyclohexyl, allyl or benzyl,
$R_2$ is hydrogen, methyl, ethyl or propyl, or
$R_1$ and $R_2$ together with the nitrogen to which they are attached form a morpholino or piperidino radical,
$R_3$ is hydrogen or lower alkyl,
$R_4$ and $R_5$ are the same dr different and each is a lower alkyl, and the dialkylaminoalkyl group is in the meta, ortho or para position,
or a pharmacologically acceptable salt thereof and a physiologically acceptable carrier therefor. Hereinafter these compounds are called compounds of the invention.

Especially preferred are pharmaceutical compositions having anticholinesterase activity in the central nervous system of mammals, wherein the dialkylaminoalkyl group is in the meta position, and $R_4$ and $R_5$ are both methyl.

Certain compounds falling within the above formula have previously been described i.e. the m disubstituted compound in which $R_1$ and $R_3 = H$ and $R_2$, $R_4$ and $R_5 =$ methyl which is known as Miotine(R) was claimed to be an insecticide and a myopic agent for use in eye drops. The m disubstituted compound in which $R_1$ and $R_2$ are methyl, $R_3$ is H and $R_4$ and $R_5$ are methyl has been described as an insecticide. The p and o disubstituted derivatives in which $R_1$ and $R_3 = H$ and $R_2$, $R_4$ and $R_5 = CH_3$ have been shown to inhibit a preparation of liver cholinesterase. The m disubstituted derivative in which $R_1=H$ and $R_2$, $R_3$, $R_4$ and $R_5=CH_3$ has also been shown to inhibit liver cholinesterase.

The remaining compounds are believed to be novel and thus the present invention also provides novel phenyl carbamate derivatives of the general formula I'

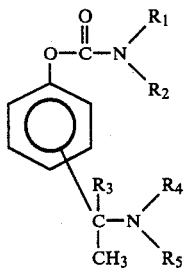

wherein
- $R_1$ is hydrogen, lower alkyl, cyclohexyl, allyl or benzyl,
- $R_2$ is hydrogen, methyl, ethyl or propyl, or
- $R_1$ and $R_2$ together with the nitrogen to which they are attached form a morpholino or piperidino radical,
- $R_3$ is hydrogen or lower alkyl,
- $R_4$ and $R_5$ are the same or different and each is a lower alkyl, and the dialkylaminoalkyl group is in the meta, ortho or para position, and pharmacologically acceptable salts thereof, provided that for compounds wherein $R_4$ and $R_5$ are both methyl and having the dialkylamino group in the meta position, when $R_2$ is methyl and $R_3$ is hydrogen, $R_1$ is neither hydrogen nor methyl, and when $R_2$ and $R_3$ are methyl, $R_1$ is not hydrogen, and for compounds wherein $R_4$ and $R_5$ are both methyl and having the dialkylamino group in the ortho or para position when $R_1$ and $R_3$ are both hydrogen $R_2$ is not methyl.

Preferred compounds of the above formula are N-ethyl-3-[1-(dimethylamino)ethyl]phenyl carbamate, N-propyl-3[1-(dimethylamino)ethyl]phenyl carbamate, N-allyl-3-[1-(dimethylamino)ethyl]phenyl carbamate, N-ethyl, N-methyl-3[1-(dimethylamino)ethyl]phenyl carbamate, N,N-diethyl-3[1-(dimethylamino)ethyl]phenyl carbamate, N-butyl-3-[1-(dimethylamino)ethyl]phenyl carbamate, N-methyl, N-propyl-3[1-(dimethylamino)ethyl]phenyl carbamate and N-ethyl, N-methyl-3[1-(dimethylamino)isopropyl]phenyl carbamate.

As indicated, the invention also includes the pharmacologically acceptable salts of these compounds such as the acetate, salicylate, fumarate, phosphate, sulphate, maleate, succinate, citrate, tartrate, propionate and butyrate salts thereof.

The compounds of formula I can be prepared by amidating a compound of formula II

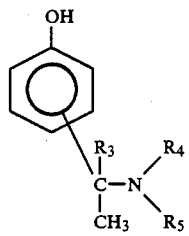

wherein $R_3$, $R_4$ and $R_5$ are as defined above.

The process can be effected in conventional manner, e.g. by reacting the compound of formula II with an appropriate isocyanate if a compound wherein $R_1$ is hydrogen is desired, or with an appropriate carbamoyl halogenide, e.g. as described below in processes A and B.

PROCESS A

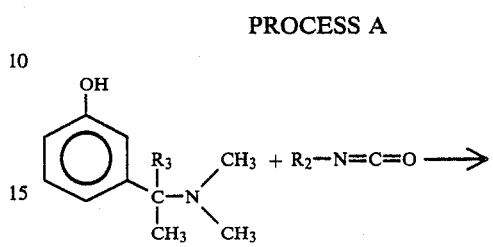

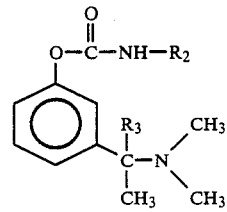

PROCESS B

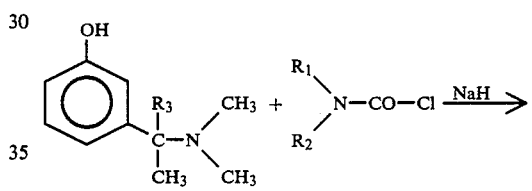

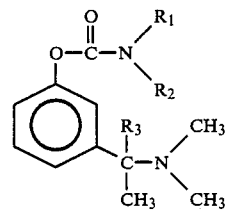

PROCESS A

A stirred suspension of α-m-Hydroxyphenylethyldimethylamine or α-m-hydroxyphenylisopropyldimethylamine in benzene (0.2–0.3 g/ml) is treated with 2.5–3 fold molar excess of the isocyanate. After stirring for 15–24 hours at ambient temperature the reaction mixture is connected to a rotovaporator (20 mm Hg). The residue obtained is dissolved in dry ether (25 ml) and the solution, which is ice cooled, is saturated with dry HCl (g). The formed precipitate (the anticipated carbamate) is filtered off, washed with dry ether (25 ml) and dried to constant weight in a dessicator over KOH pellets under high vacuum (0.1 mm Hg).

PROCESS B

A solution of α-m-hydroxyphenylethyldimethylamine or α-m-hydroxyphenylisopropyldimethylamine in dry acetonitrile (0.1–0.5M) is reacted with 50–70% molar excess of the corresponding carbamoyl chloride in the presence of 200% molar excess of NaH dispersion (50–80% in mineral oil). The reaction mixture is left to stir at ambient temperature for 15-24 hours. Removal of the acetonitrile under reduced pressure (20 mm Hg) is followed by the addition of water (10-25 ml). The pH of the aqueous solution is adjusted to pH=11 by the addition of the appropriate amount of NaOH 0.1N followed by extraction with ether (3×25 ml). The combined organic phases are washed with brine (25 ml) dried over MgSO$_4$ anhydride which is then filtered off. The ice cooled etheral filtrate is saturated with a stream of HCl (g) resulting in the formation of a heavy precipitate (the anticipated carbamate) which is collected by filtration, washed with dry ether (20 ml) and dried to constant weight in a desiccator under high vacuum (0.1 mm Hg) over KOH pellets.

The compounds of the invention e.g. in free form or salt form can be utilized by formulating one or more of them in compositions such as tablets, capsules or elixirs for oral administration or in sterile solutions or suspensions for parenteral administration. A compound or mixture of compounds of formula (I) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavour.

Sterile compositions for injection can be formulated according to conventional pharmaceutical practice by dissolving or suspending the active substance in a vehicle such as water for injection. Buffers, preservatives, antioxidants and the like can be incorporated as required.

Preferred antioxidants for use with the compounds of the present invention include sodium metabisulphite and ascorbic acid.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars described are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

0.5 g (3.03 mmole) of α-m-hydroxyphenylethyldimethylamine are dissolved in 15 ml of dry acetonitrile and 0.70 g (5.2 mmole) of diethylcarbamoylchloride are added to the mixture with stirring. This is followed by NaH 150 mg (50%) of dispersion. The reaction mixture is stirred overnight at 25°-30° C. Removal of acetonitrile under reduced pressure is followed by addition of water (10 ml) and adjustment of the pH to 11. The product is extracted in ether, which is washed by brine, dried over MgSO$_4$ and filtered. Upon addition of HCl (g) precipitation occurs immediately, the product is filtered off, washed by dry ether and dried in a desiccator under high vacuum over KOH pellets.

The carbamate is obtained as a white powder 640 mg (80%) mp. 137°-138° and identified as N,N-diethyl-3-[1-(dimethylamino)ethyl]phenyl carbamate, having the formula

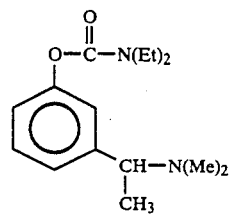

EXAMPLE 2

0.75 g (4.55 mmol) of α-m-hydroxyphenylethyldimethylamine are suspended in benzene (3 ml) and 0.898 g of ethylisocyanate are added to the mixture with stirring. After stirring 12 hours at room temperature the solvent is removed under reduced pressure.

The residue obtained was dissolved in dry ether. Introduction of dry HCl gas into the reaction mixture causes a heavy precipitation. The product is filtered off, washed with ether and dried in a desiccator over KOH pellets. The carbamate is obtained as a white powder 800 mg (75%) mp. 177°-179° C. and identified as N-ethyl-3[1-(dimethylamino)ethyl]phenyl carbamate having the formula

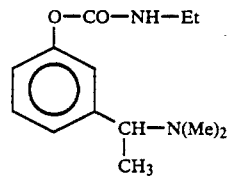

The compounds of the present invention are useful as pharmaceuticals. In particular they show the following activities in vitro and in vivo in the tests specified below.

The values are correct when taken in comparison with the standard drug physostigmine.

IN VITRO EXPERIMENTS

Tests for anticholinesterase activity

A solubilized preparation of acetylcholinesterase was prepared from mouse whole brain (minus cerebellum). The brain was homogenized with (100 mg/ml) phosphate buffer; pH 8.0, centrifuged, the supernatant discarded, and the pellet mixed with a similar volume as above of buffer pH 8.0 plus 1% Triton; mixed, centrifuged and the supernatant which contained most of the solubilized enzyme, was used for the subsequent determinations of anticholinesterase activity.

The activity of the enzyme (rate of hydrolysis of substrate, acetylthiocholine) was measured using at least 4 different concentrations of substrate, and at least 3 different concentrations of each inhibitor. The enzyme was incubated with inhibitor for periods ranging for 2-180 mins. at 37° C., substrate was then added, and its rate of hydrolysis measured by the spectrophotometric method of Ellman et al. (1961).

The molar concentration of each agent that inhibited the activity of the enzyme by 50% ($IC_{50}$) at the peak time of activity (15-60 min) was calculated from this data and recorded in Table 1 hereinafter. The compounds in general produce a significant inhibition from about $10^{-5}$ to about $10^{-8}$ molar.

IN VIVO EXPERIMENTS (a) Assessment of acetylcholinesterase inhibition

The effect of each compound on brain acetylcholinesterase in vivo was measured, after subcutaneous or oral administration to mice. Animals were sacrificed, at different times ranging from 0.25-8 hours after drug administration. The brain was rapidly removed, and the enzyme acetylcholinesterase extracted and solubilized with 0.1% Triton, and its ability to hydrolyse acetylthiocholine assessed as described above (in vitro experiments), in comparison with the enzyme removed from mice injected with normal saline. The compounds have in general a potency of from about 2% to about 90% that of physostigmine.

(b) Assessment of acute toxicity

Mice were given one of at least three different doses of each compound, orally or subcutaneously, a minimum of 10 mice allotted to each dose. The number of animals which died at each dose within 3 hours was determined. From these data, the $LD_{50}$ (dose in mg/kg which was lethal to 50% of the mice) was computed.

This experiment was repeated after the animals had been pretreated with atropine sulphate, which blocks both peripheral and central muscarinic receptors. The data from these experiments enabled the assessment of the relative degrees of toxicity of the carbamates which result from excessive activation of muscarinic receptors, and from respiratory muscle paralysis, which is insensitive to this blocking agent.

The incidence and degree of side effects was noted for each dose of drug, starting with the lowest that caused any significant (>20%) inhibition of whole brain acetylcholinesterase.

(c) Antagonism of the somnolent and respiratory depressant effects of opiates

Different doses of the carbamate compounds were injected intravenously with morphine in rabbits Respiration rate, arterial blood gas tensions and pH were monitored continuously before and after drug administration for 4-5 hours. In another series of experiments the effect of the anticholinesterase drugs was assessed on the analgesic effect of opiates in rabbits after application of a nociceptive stimulus, i.e. electrical stimulation of the sciatic nerve.

All specific examples of formula I' mentioned hereinbefore, e.g. on specification page 10, and after especially Tables 1 to 3, are prepared in analogous manner to Example 1 when $R_1$ and $R_2$ are each other than hydrogen and Example 2 when one of $R_1$ and $R_2$ are hydrogen. They are thus obtained as hydrochloride salts (except where otherwise specified). The specific compounds have metal substitutions.

TABLE 1

In vitro activity on solubilized mouse brain enzyme

| Compound ($R_4 = R_5 = CH_3$) | $R_1$ | $R_2$ | $R_3$ | $IC_{50}(M)$ | Time of peak activity (mins) |
|---|---|---|---|---|---|
| Physiostigmine (Salicylate) | H | $CH_3$ | H | $1.1 \times 10^{-8}$ | 30 |
| Miotine HCl | H | $CH_3$ | H | $1.3 \times 10^{-8}$ | 30 |
| $RA_6$ HCl | H | $C_2H_5$ | H | $4.0 \times 10^{-7}$ | 120 |
| $RA_{15}$ HCl | H | $C_3H_7$ n-propyl | H | $1.1 \times 10^{-7}$ | 120 |
| $RA_{14}$ HCl | H | $C_3H_5$ allyl | H | $4.3 \times 10^{-7}$ | 120 |
| $RA_{13}$ HCl | H | $C_3H_7$ isopropy | H | $1.2 \times 10^{-5}$ | 120 |
| $RA_5$ HCl | H | $C_4H_9$ n-butyl | H | $7.6 \times 10^{-8}$ | 120 |
| $RA_{12}$ | H | cyclohexyl | H | $9.3 \times 10^{-8}$ | 120 |
| $RA_{10}$ HCl | $CH_3$ | $CH_3$ | H | $2.7 \times 10^{-8}$ | 120 |
| $RA_7$ HCl | $CH_3$ | $C_2H_5$ | H | $1.3 \times 10^{-6}$ | 90 |
| $RA_8$ HCl | $C_2H_5$ | $C_2H_5$ | H | $3.5 \times 10^{-5}$ | 30 |
| $RA_{11}$ HCl | | morpholino | H | $>2 \times 10^{-5}$ | 30 |
| $RA_4$ HCl | $CH_3$ | propyl | H | $1.7 \times 10^{-6}$ | 60 |

Melting points of compounds (all in the hydrochloride form except for $RA_{12}$ which is in the free base form as it precipitated from the reaction mixture before addition of hydrogen chloride) are in degrees Centigrade: $RA_6$ 167-170; $RA_{15}$ 141-143; $RA_{14}$ 147-152; $RA_{13}$ 146-148; $RA_5$ 158-162; $RA_{12}$ 75-77; $RA_{10}$ 145; $RA_7$ 135-136; $RA_8$ 137-138; $RA_{11}$ amorphous; $RA_4$ 148-149.

Compound $RA_{11}$ has an RF value of 0.59 in a system of 95 parts of ethyl acetate and 5 parts of 33% (w/w) dimethylamine in ethanol.

TABLE 2

Anticholinesterase activity of compounds in mouse brain compared to that of physostigmine

| Compound | Relative potency to physostigmine after subcut. (s.c.) administration | Relative potency to physostigmine after oral administration | % cholinesterase inhibition 3 hours after s.c. administration |
|---|---|---|---|
| Physostigmine | 100 | 100 | 0 |
| Miotine | 100 | 300 | 5 |
| $RA_6$ | 11 | 19 | 35 |
| $RA_{15}$ | 33 | 32 | 37 |
| $RA_{14}$ | 15 | 22 | 35 |
| $RA_{13}$ | 2 | 5 | — |
| $RA_5$ | 36 | 29 | 30 |
| $RA_{12}$ | 13 | 17 | 37 |
| $RA_{10}$ | 81 | 92 | 7 |
| $RA_7$ | 25 | 57 | 41 |
| $RA_8$ | 2 | 5 | 32 |
| $RA_4$ | 13 | 29 | 25 |

TABLE 3

Acute toxicity of carbamates in mice

| Compound | $LD_{50}$ μmoles/ kg s.c. | Degree of* protection afforded by pretreatment with atropine | Therapeutic ratio $LD_{50}/ED_{50}$ s.c. | $\dfrac{LD_{50} \text{ oral}}{LD_{50} \text{ s.c.}}$ |
|---|---|---|---|---|
| Physostigmine | 3.0 | 3.0 | 3.3 | 4.1 |
| Miotine | 4.5 | 2.4 | 4.9 | 1.2 |
| $RA_6$ | 96 | 2.6 | 11.9 | 2.1 |

TABLE 3-continued

| | Acute toxicity of carbamates in mice | | | |
|---|---|---|---|---|
| Compound | $LD_{50}$ μmoles/ kg s.c. | Degree of* protection afforded by pretreatment with atropine | Therapeutic ratio $LD_{50}/ED_{50}$ s.c. | $\dfrac{LD_{50} \text{ oral}}{LD_{50} \text{ s.c.}}$ |
| $RA_{15}$ | 31 | 4.1 | 11.1 | 4.5 |
| $RA_{14}$ | 69 | 8.0 | 11.5 | 4.4 |
| $RA_{13}$ | 65 | 4.5 | 1.6 | 1.1 |
| $RA_5$ | 19 | 5.8 | 7.6 | 5.0 |
| $RA_{12}$ | 42 | 3.8 | 5.8 | 3.6 |
| $RA_{10}$ | 14 | 5.0 | 12.7 | 9.7 |
| $RA_7$ | 46 | 10.4 | 12.4 | 1.2 |
| $RA_8$ | >568 | — | >10.0 | — |
| $RA_4$ | 72 | 4.9 | 10.0 | 1.7 |

*Ratio of $LD_{50}$ after pretreatment with atropine sulphate 5 mg/kg to $LD_{50}$ of drug alone.

The data in Tables 1 and 2 demonstrate that somewhat larger quantities are required of all the drugs of the RA series than of physostigmine to inhibit the enzyme acetylcholinesterase. However, a comparison of the data in Table 1 with that in Table 2, shows that compounds $RA_5$, $RA_6$, $RA_{15}$, $RA_{14}$, $RA_{10}$, $RA_7$ and $RA_8$ are all relatively more active in vivo compared to physostigmine than one would expect from the in vitro data. This greater in vivo potency is particularly marked when the drugs are administered orally. This relatively greater in vivo activity may be due to:
 (a) greater chemical stability
 (b) a slower metabolic degradation or/and excretion
 (c) a higher lipid solubility, enabling a greater proportion of the drug to gain access to the enzyme in the central nervous system
 (d) more efficient absorption from gastro-intestinal tract.

For the purposes of their therapeutic application it is of little importance if one needs to give the drug (to human subjects) at a dose of 1–2 mg (physostigmine) or 2–50 mg that may be required of the compounds of the RA series. What is important is the safety of the drugs and the presence and severity of side effects that may occur at therapeutic doses. A commonly-used measure of drug safety is the therapeutic index—or $LD_{50}/ED_{50}$ $$\dfrac{\text{Dose to kill 50\% of animals}}{\text{Dose to cause the desired therapeutic effect}}$$

It is assumed that the therapeutic effect of these anticholinesterase agents results from an elevation of brain cholinergic activity. This in turn, should be related to the degree of inhibition of acetylcholinesterase. For the purpose of the computation of the denominator of the therapeutic ratio, there is used the dose of drug that inhibits the activity of acetylcholinesterase by 50%. This is based on the observation by Thal et al. (Ann. Neurology 13: 491, 1983) that the maximum improvement in short term memory obtained in a series of patients with Alzheimer's disease was achieved with a dose of physostigmine which blocked the acetylcholinesterase in the cerebro-spinal fluid by 50%. The numerator is the dose found to kill 50% of the animals within 4 hours of a subcutaneous injection. The therapeutic ratios of compounds $RA^4$, 5, 6, 7, 8, 10, 14 and 15 are all significantly higher than of physostigmine (see Table 3). This indicates that all these compounds have a wider margin of safety than that of physostigmine. Moreover, these RA compounds do not produce any significant undesirable side effects such as defaecation, lachrymation, fasciculations or tremor at the doses which inhibit the brain enzyme by 50%, while the former 3 side effects are clearly evident when physostigmine is given at the appropriate dose ($ED_{50}$).

The data in Table 3 show that atropine can afford considerably greater protection against the lethality of the derivatives $RA^4$, 5, 7, 10, 13 and 14. This is particularly important in the treatment of drug overdose since the respiratory muscle paralysis which is not affected by atropine and which is the cause of death induced by excess drug administration in the presence of atropine cannot be satisfactorily reversed by specific antidotes.

The duration of significant brain enzyme inhibition (>30%) induced by physostigmine ($ED_{50}$ dose) is less than 2 hours. Compounds $RA_4$, 5, 6, 7, 8, 12, 14, 15 all act for more than 3 hours at their respective $ED_{50}$ doses and $RA_6$ and $RA_7$ still causes significant inhibition (36%) after 7 hours. Since none of these drugs caused noticeable side effects at the $ED_{50}$ doses, an even longer duration of action may be achieved by giving between 50 and 100% larger doses. The longer duration of action is a distinct advantage, particularly if the drugs are to be administered chronically to subjects suffering from neurological and behavioural conditions associated with a deficit in cholinergic transmission in the central nervous system, e.g. Alzheimer's disease, tardive dyskinesias, Huntingdon's chorea, Down's syndrome and Friedrich's ataxia.

The better the absorption of the drug after oral administration the more closely the $LD_{50}$ given by this route resembles that after subcutaneous injection. Table 3 shows that $RA_6$, 13, 7 and 4 are more efficiently absorbed from the gastro-intestinal tract than is physostigmine. The $ED_{50}$ of $RA_8$ after oral administration is the same as that after S.C. injection, indicating a much better oral bioavailability than that of physostigmine. The higher oral bioavailability of these compounds may be a considerable advantage for their clinical use.

$RA_{10}$, $RA_6$, $RA_{14}$ and $RA_{15}$ produce significant antagonism of the respiratory depressant effects of morphine in rabbits for periods lasting between 3–5 hours depending on the drug and the dose administered. The analgesic activity of morphine is not reduced by the RA compounds. Muscle fasciculations are not evident at the doses of drugs administered. Physostigmine (0.1–0.2 mg/kg) antagonizes the respiratory depressant effect of morphine for 30–60 mins only and fasciculations are marked at the higher dose.

These findings show that the RA compounds may be given together with morphine to obtain adequate analgesia without significant degrees of respiratory depression.

The most preferred compounds of the RA series are $RA_4$, $RA_5$, $RA_6$, $RA_{15}$, $RA_{14}$, $RA_7$ and $RA_8$, all of which produce inhibition of brain acetylcholinesterase after parenteral administration of significantly longer duration than that induced by physostigmine or miotine. These compounds also have a greater safety margin (therapeutic ratio) than physostigmine. $RA_4$, 6, 7 and 8 also show better bioavailability after oral administration than physostigmine. In addition, the acute toxicity (lethality) induced by $RA_7$ can be decreased more than 10-fold and that of $RA_{14}$ more than 8-fold by the antidote atropine, compared to only a 3-fold decrease for physostigmine and miotine.

The compounds of the invention are therefore useful for the treatment of senile dementia, Alzheimer's disease, Huntingdon's chorea, tardive dyskinesias, hyperkinesia, mania, acute confusion disorders, Down's syndrome and Friedrich's ataxia.

For these indications, the exact dosage will of course vary depending upon the compound employed, mode of administration and treatment desired. The compounds may be administered by any conventional route, non-oral or preferably orally.

In general, satisfactory results are obtained when administered at a daily dosage of from about 0.05 to 10 mg/kg animal body weight. For the larger mammals, an indicated total daily dosage is in the range from about 0.5 to about 25 mg of the compound, conveniently administered in divided doses 2 to 4 times a day in unit dosage form containing for example from about 0.1 to about 12 mg of the compound or in sustained release form.

The compounds may be administered in similar manner to known standards for use in these utilities. The suitable daily dosage for a particular compound will depend on a number of factors such as its relative potency of activity.

The compounds according to the invention may be administered in free base form or as a pharmaceutically acceptable acid addition salt. Such salts may be prepared in conventional manner and exhibit the same order of activity as the free forms.

It will be evident to those skilled in the art that the invention is not limited to the details of the foregoing illustrative embodiments and examples and that the present invention may be embodied in other specific forms without departing from the essential attributes thereof, and it is, therefore, desired that the present embodiments and examples be considered in all respects as illustrative and not restrictive, reference being made to the appended claims, rather than to the foregoing description, and all changes which come with the meaning and range of equivalency of the claims are, therefore, intended to be embraced therein.

What is claimed is:

1. N-cyclohexyl-3-[1-(dimethylamino)ethyl]phenyl carbamate and pharmacologically acceptable salts thereof.

2. N-allyl-3-[1-(dimethylamino)ethyl]phenyl carbamate and pharmacologically acceptable salts thereof.

3. N-ethyl, N-methyl-3-[1-(dimethylamino)ethyl]phenyl carbamate and pharmacologically acceptable salts thereof.

4. A method of treating a subject suffering from senile dementia, Alzhemier's disease, Huntingdon's chorea, tardive dyskinesias,, hyperkinesia, mania, acute confusion disorders, Friedrich's ataxia and Down's syndrome, which comprises administering to such a subject a therapeutically effective amount of a compound selected from the group consisting of N-cyclohexyl-3-[1-(dimethylamino)ethyl]phenyl carbamate, N-allyl-3-[1-(dimethylamino)ethyl]phenyl carbamate, N-ethyl, N-methyl-3[1-(dimethylamino)ethyl]phenyl carbamate, and pharmacologically acceptable salts thereof.

* * * * *